United States Patent
Chen

(10) Patent No.: US 11,414,696 B1
(45) Date of Patent: Aug. 16, 2022

(54) SPATIALLY BARCODED MICROARRAY

(71) Applicant: WellSIM Biomedical Technologies, Inc., Berkeley, CA (US)

(72) Inventor: Yuchao Chen, Berkeley, CA (US)

(73) Assignee: WELLSIM BIOMEDICAL TECHNOLOGIES, INC., Berkeley, CA (US)

( * ) Notice: Subject to any disclaimer, the term of this patent is extended or adjusted under 35 U.S.C. 154(b) by 0 days.

(21) Appl. No.: 17/469,897

(22) Filed: Sep. 9, 2021

Related U.S. Application Data

(60) Provisional application No. 63/213,681, filed on Jun. 22, 2021.

(51) Int. Cl.
*C12Q 1/6837* (2018.01)

(52) U.S. Cl.
CPC .................................. *C12Q 1/6837* (2013.01)

(58) Field of Classification Search
CPC .................................................. C12Q 1/6837
See application file for complete search history.

(56) References Cited

PUBLICATIONS

Ehrlich et al. (Analytical Biochemistry 399 (2010) 251-256).*
Yousefi H, et al., Producing Covalent Microarrays of Amine-Conjugated DNA Probes on Various Functional Surfaces to Create Stable and Reliable Biosensors, Adv. Mater. Interfaces (2018) 1800659.
Qin WW, et al., A successive laminar flow extraction for plant medicine preparation by microfluidic chip, Microfluidics and Nanofluidics (2019) 23:61.
Liu Y, et al., High-Spatial-Resolution Multi-Omics Sequencing via Deterministic Barcoding in Tissue, Cell (2020) 183: 1665-1681.
Oguchi Y, et al., Development of a sequencing system for spatial decoding of DNA barcode molecules at single-molecule resolution, Communications Biology (2020) 3:788.
Salmen F, et al., Barcoded solid-phase RNA capture for Spatial Transcriptomics profiling in mammalian tissue sections, Nature Protocol (2018) 13(11):2501-2534.

* cited by examiner

*Primary Examiner* — Robert H Havlin
(74) *Attorney, Agent, or Firm* — Jun He Law Offices P.C.; Yi Zhang

(57) ABSTRACT

The present disclosure provides a microarray comprising a plurality of probes. Each probe comprises a first oligonucleotide and a second oligonucleotide. The location of each probe on the microarray can be determined by the length of the first oligonucleotide and the length of the second oligonucleotide, thus providing a spatially barcoded microarray. Also provided are the methods of producing such spatially barcoded microarray. Also provided are the method of using such spatially barcoded microarray.

12 Claims, 11 Drawing Sheets

SPATIALLY BARCODED MICROARRAY

CROSS-REFERENCE TO RELATED APPLICATIONS

This application claims the priority to U.S. provisional patent application No. 63/213,681 filed Jun. 22, 2021, the entire disclosure of which is incorporated herein by reference.

FIELD OF THE INVENTION

The present invention generally relates to molecular biology and assays. More particularly, the invention relates to compositions and assays for determining spatial distributions of a large number of biological molecules in a solid sample.

BACKGROUND OF THE INVENTION

The relationship between gene activities and where the activities occur within a tissue is critical to understanding normal development and disease pathology. Spatial transcriptomics is a groundbreaking molecular profiling technology that reveals both the RNA sequence and their spatial locations in a tissue sample by capturing tissue RNA using a spatially barcoded microarray. Fabrication of a microarray with spatially barcoded capture probes is critical for the success of spatial transcriptomics.

Currently, spatial barcoding is achieved by several technologies, including microspotting of nucleotides, array of split-pool-barcoded beads, microfluidic channels, or in-situ solid-phase amplification. These spatial barcoding technologies, however, have several limitations.

The methods based on microspotting or microfluidic channels have limited resolutions. The split-pool-barcoded beads method, though has a higher resolution, requires a decoding process which is time consuming and uses specific costly equipment. The method based on in-situ solid-phase amplification is complicated and expensive.

Therefore, there is a continuing need to develop new spatially barcoded microarrays that are less expensive, easy to fabricate, flexible in the array dimension and resolution, and highly scalable.

BRIEF SUMMARY OF THE INVENTION

In one aspect, the present disclosure provides a spatially barcoded microarray. In some embodiments, the spatially barcoded microarray comprises:
  a solid substrate having a surface; and
  an array of N probes immobilized on the surface, wherein
    each probe comprises a barcode region comprising a first barcode oligonucleotide linked to a second barcode oligonucleotide,
  wherein for any pair of the probes consisting of an ith probe and a jth probe ($1<<i<j<<N$),
    the ith probe comprises the first barcode oligonucleotide $A_i$ linked to the second barcode oligonucleotide $B_i$, and
    the jth oligonucleotide comprises the first barcode oligonucleotide $A_j$ linked to the second barcode oligonucleotide
  wherein
    the ith probe has a location of ($X_i$, $Y_i$) under an X-Y axis on the surface, and the jth oligonucleotide has a location of ($X_j$, $Y_j$) under the X-Y axis on the surface,
  wherein
    if $X_i$ is larger than $X_j$, then the barcode oligonucleotide $A_i$ is longer than the barcode oligonucleotide $A_j$, and
    if $Y_i$ is larger than $Y_j$, then the barcode oligonucleotide $B_i$ is longer than the barcode oligonucleotide $B_j$, and
  wherein the length of the barcode oligonucleotides $A_i$ and $B_i$, and the length of the barcode oligonucleotides $A_j$ and $B_j$ identify the locations of the ith and the jth probes on the surface, respectively.

In some embodiments, each probe further comprises a capture oligonucleotide.

In some embodiments, in each probe the first barcode oligonucleotide is linked to the 3' end of the second barcode oligonucleotide. In some embodiments, in each probe the first barcode oligonucleotide is linked to the 5' end of the second barcode oligonucleotide.

In some embodiments, the sequence of the barcode oligonucleotide $A_i$ comprises the sequence of the barcode oligonucleotide $A_j$, or vice versa. In some embodiments, the sequence of the barcode oligonucleotide $B_i$ comprises the sequence of the barcode tag $B_j$, or vice versa.

In some embodiments, N is larger 100, 1,000, 10,000, 10,000, or 1,000,000.

In some embodiments, each probe has a free 3' end of a nucleotide.

In some embodiments, each probe further comprises a cleavage domain, a functional domain, and a unique probe identifier, or a combination thereof.

In another aspect, the present disclosure provides a method for generating a spatially barcoded microarray. In some embodiments, the method comprises:
  (a) providing (i) a solid substrate comprising a surface, and (ii) a plurality of first oligonucleotides immobilized on the surface;
  (b) exposing the plurality of the first oligonucleotides to a fluidic flow, wherein the fluidic flow comprises a first liquid and a second liquid that flow along a first direction, wherein the first liquid and the second liquid are immiscible with each other and form an interface parallel to a first direction, wherein the first liquid comprises a first enzyme capable of removing one or more nucleotides from the first oligonucleotides; and
  (c) adjusting the relative proportion of the first liquid and the second liquid in the fluidic flow to allow the number of the first oligonucleotides that are exposed to the first liquid changes along with time, wherein the number of the one or more nucleotides that are removed from each of the first oligonucleotides correlates with the timespan in which each of the first oligonucleotides is exposed to the first liquid, thereby generating a plurality of probes each having a segment of the first oligonucleotides, wherein the length of the segments of the first oligonucleotides forms a gradient perpendicular to the first direction.

In some embodiments, the method further comprises adding a second oligonucleotide to the free end of each probe. In some embodiments, the second oligonucleotide is added by a first ligase enzyme.

In some embodiments, the method further comprises exposing the plurality of probes to a second fluidic flow comprises a third liquid and a fourth liquid that flow along a second direction, wherein the third liquid and the fourth liquid are immiscible with each other and form an interface parallel to the second direction, wherein the third liquid comprises a second enzyme capable of shortening the probes by removing one or more nucleotides from the second oligonucleotides. In some embodiments, the second direction and the first direction form an angle of 90° or 270°.

In some embodiments, the method comprises adjusting the relative proportion of the third liquid and the fourth liquid in the fluidic flow to allow the number of the probes that are exposed to the third liquid changes along with time, wherein the number of the one or more nucleotides that are removed from the second oligonucleotides correlates with the timespan in which each probe is exposed to the third liquid, thereby generating a microarray spatially barcoded by the length of the segment of the first oligonucleotide and the segment of the second oligonucleotide comprised in each probe.

In some embodiments, none of the first oligonucleotides or the second oligonucleotides is completed removed from any of the probes In some embodiments, the first or second enzyme capable of shortening probe is an exonuclease. In some embodiments, the exonuclease is selected from Exonuclease I, Exonuclease III, Exonuclease V, Exonuclease VII, Exonuclease VIII, Exonuclease T, T5 Exonuclease, T7 Exonuclease, Lambda Exonuclease, and a combination thereof.

In some embodiments, the method further comprises adding a target capture oligonucleotide to the free end of the second oligonucleotide. In some embodiments, the target capture oligonucleotide is added by a second ligase enzyme.

In some embodiments, the microarray has one or more microfluidic channels and wherein the flow rate of the first liquid and the flow rate of the second liquid are controlled by one or more pump modules.

In some embodiments, the first or third liquid is aqueous phase and the second or fourth liquid is organic phase.

In some embodiments, the method for generating a spatially barcoded microarray comprises:
a) providing (i) a solid substrate comprising a surface, and (ii) a plurality of first oligonucleotides immobilized on the surface;
b) exposing the plurality of the first oligonucleotides to a first concentration gradient of a first enzyme, wherein the first concentration gradient of the first enzyme varies along a first direction; and
c) removing one or more nucleotides from the first oligonucleotides by the first enzyme, wherein the number of the one or more nucleotides that are removed from the first oligonucleotides correlates with the concentration of the first enzyme at the location of each probe on the surface, thereby generating a plurality of probes each having a segment of the first oligonucleotides, wherein the length of the segments of the first oligonucleotides forms a gradient perpendicular to the first direction.

In some embodiments, the method further comprises a second oligonucleotide to the free end of each probe. In some embodiments, the second oligonucleotide is added by a first ligase enzyme.

In some embodiments, the method further comprises exposing the plurality of probes to a second concentration gradient of a second enzyme capable of removing one or more nucleotides from the second oligonucleotides, wherein the second concentration gradient of the second enzyme varies along a second direction. In some embodiments, the second direction and the first direction form an angle of 90° or 270°.

In some embodiments, the number of the one or more nucleotides that are removed from the second oligonucleotides by the second enzyme correlates with the concentration of the second enzyme at the location of each probe on the surface.

In some embodiments, none of the first oligonucleotides or the second oligonucleotides is completed removed from any of the probes.

In some embodiments, the first or second enzyme capable of shortening an oligonucleotide is an exonuclease. In some embodiments, the exonuclease is selected from Exonuclease I, Exonuclease III, Exonuclease V, Exonuclease VII, Exonuclease VIII, Exonuclease T, T5 Exonuclease, T7 Exonuclease, Lambda Exonuclease and a combination thereof.

In some embodiments, the method further comprises adding a poly-dT oligonucleotide to the free end of the second oligonucleotide.

In another aspect, the present disclosure provides a method for measuring a nucleic acid target in a sample. In one embodiment, the method comprises:
contacting the sample with a spatially barcoded microarray, wherein the spatially barcoded microarray comprises:
a solid substrate having a surface; and
an array of N probes immobilized on the surface, wherein each probe comprises a capture region capable of specific binding to the biological target and a barcode region,
wherein for any pair of the probes consisting of an ith probe and a jth probe ($1<<i<j<<N$),
the barcode region of the ith probe comprises a first barcode oligonucleotide $A_i$ linked to a second barcode oligonucleotide $B_i$, and
the barcode region of the jth probe comprises a first barcode oligonucleotide $A_j$ linked to a second barcode oligonucleotide $B_j$,
wherein
the ith probe has a location of $(X_i, Y_i)$ under an X-Y axis on the surface, and
the jth oligonucleotide has a location of $(X_j, Y_j)$ under the X-Y axis on the surface,
wherein
if $X_i$ is larger than $X_j$, then the barcode oligonucleotide $A_i$ is longer than the barcode oligonucleotide $A_j$, and
if $Y_i$ is larger than $Y_j$, then the barcode oligonucleotide $B_i$ is longer than the barcode oligonucleotide $B_j$;
allowing the probes to interact with the nucleic acid target;
extending the probes specifically binding to the nucleic acid target to generate a plurality of extended products; and
sequencing the plurality of extended products to determine the length of the first barcode oligonucleotide and the length of the second barcode oligonucleotide, thereby identifying the location of the nucleic acid target in the sample.

In some embodiments, the nucleic acid target is mRNA.

In some embodiments, the capture region has a sequence complementary to the sequence of the nucleic acid target. In some embodiments, the capture region hybridizes with the nucleic acid target. In some embodiments, the capture region capable of specific binding to the nucleic acid target is poly-dT.

In some embodiments, the method further comprises a step of amplifying the extended products before the sequencing step.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION OF THE INVENTION

Figure 1:
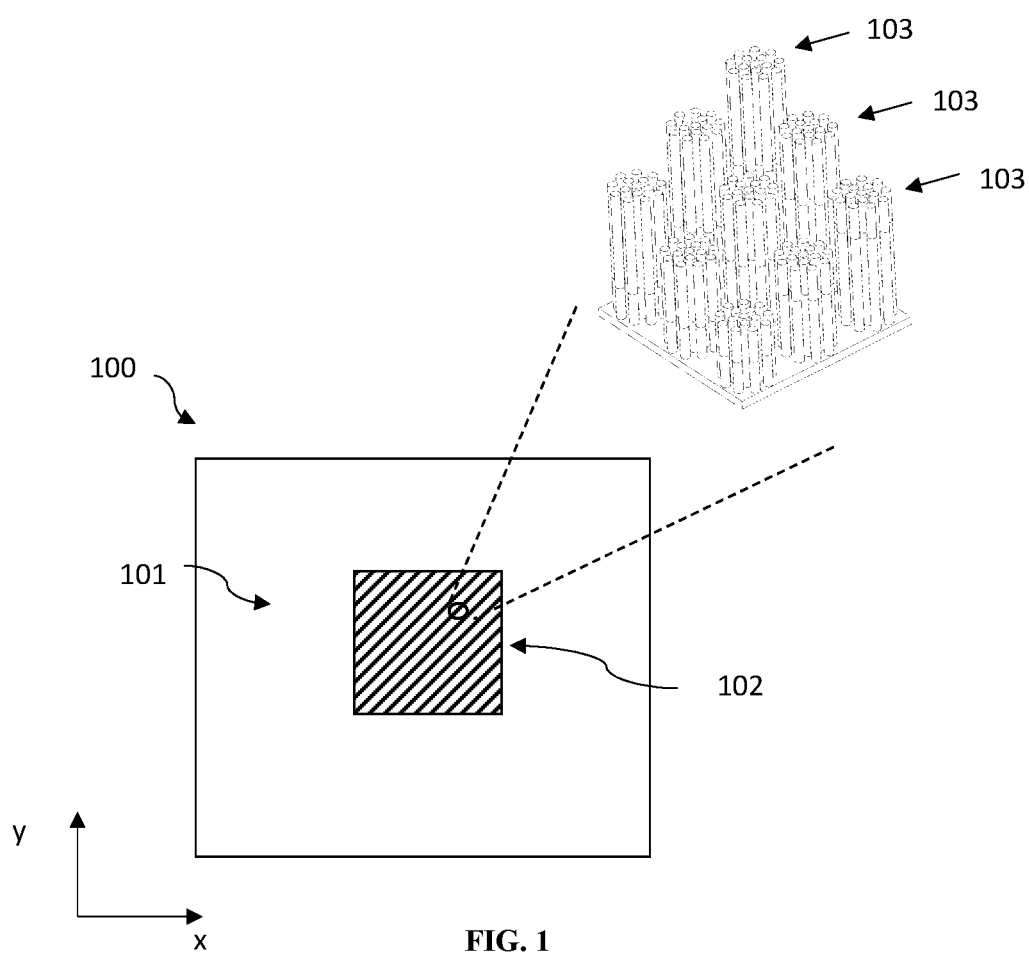
FIG. 1 shows a spatially barcoded microarray according to an embodiment of the invention.

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, the embodiments described herein can be practiced without there specific details. In other instances, methods, procedures and components have not been described in detail so as not to obscure the related relevant function being described. Also, the description is not to be considered as limiting the scope of the implementations described herein. It will be understood that descriptions and characterizations of the embodiments set forth in this disclosure are not to be considered as mutually exclusive, unless otherwise noted.

Definition

The following definitions are used in the disclosure:

It is understood that as used herein and in the appended claims, the singular forms "a," "an," and "the" include the plural reference unless the context clearly dictates otherwise. Thus, for example, a reference to a "bridge probe" is a reference to one or more bridge probes, and includes equivalents thereof known to those skilled in the art and so forth.

As used herein, "associate" or "associating" means physically direct or indirect attachment. For example, the label probe can hybridize to one or more bridge probe, which hybridizes to the target probe, which hybridizes the target nucleic acid, thereby the label probe is associated with the target nucleic acid.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 4 to 20 nucleotides means a range whose lower limit is 4 nucleotides, and whose upper limit is 20 nucleotides.

The term "complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%>, 70%>, 80%>, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

The term "hybridizing" refers to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences in a mixed population (e.g., a cell lysate or DNA preparation from a tissue biopsy). A "stringent hybridization" and "stringent hybridization wash conditions" in the context of nucleic acid hybridization (e.g., as in array, microarray, Southern or northern hybridizations) are sequence dependent, and are different under different environmental parameters. An extensive guide to the hybridization of nucleic acids is found in, e.g., Tijssen *Laboratory Techniques in Biochemistry and Molecular Biology—Hybridization with Nucleic Acid Probes part I, Ch. 2, "Overview of principles of hybridization and the strategy of nucleic acid probe assays,"* (1993) Elsevier, N.Y. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook and Russell *Molecular Cloning: A Laboratory Manual* (3rd ed.) Vol. 1-3 (2001) Cold Spring Harbor Laboratory, Cold Spring Harbor Press, NY). An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4×SSC to 6×SSC at 40° C. for 15 minutes.

The term "location" as used herein may refer to a two-dimensional region or a three-dimensional region. Suitably a region can be of any size. Suitably the maximum size of the region may be determined by the properties of the microarray and/or the particular tissue or substrate used in the method. Suitably a location of interest may be any region, suitably any region on a substrate. Suitably, a location of interest is a two-dimensional region. Suitably a location of interest may be between 1 $pm^2$-150 $mm^2$ in size, suitably between 1 $pm^2$-1 $mm^2$ in size, suitably between 1 $pm^2$-1,000,000 $pm^2$ in size, suitably between 1 $pm^2$-200,000 $pm^2$ in size, suitably between 1 $pm^2$-20,000 $pm^2$ in size, suitably between 1 $pm^7$-1000 $pm^2$ in size.

The term "nucleic acid" (interchangeable with the term "polynucleotide") as used herein refers to any polymer formed of a plurality of nucleotide bases, wherein the bases may be comprised of canonical or non-canonical bases, and wherein the backbone may be modified or unmodified, and wherein the nucleotides may be linked by conventional phosphodiester bonds, or non-conventional bonds such as phosphorothioate bonds or chemical bonds. The polynucleotide can additionally comprise non-nucleotide elements such as labels, quenchers, blocking groups, or the like. The polynucleotide can be, e.g., single-stranded or double-stranded.

A "nucleic acid target" or "target nucleic acid" means a nucleic acid, or optionally a region thereof, that is to be detected. The target nucleic acid can have a nucleic acid sequence existing in the nature or any sequence designed and generated by human. For example, the nucleic acid sequence can be a genomic sequence of a prokaryotic or eukaryotic species. A prokaryotic species includes, for example, bacteria. A eukaryotic species includes, for example, a fungus, a plant, an animal, e.g., a mammal. In particular, the sequence of a target nucleic acid of interest can be found in public available databases, for example, the database of National Center for Biotechnology Information. The target nucleic acid can be single-stranded or double stranded. In certain embodiments, the target nucleic acid is a single stranded nucleotide polymer. In certain embodiments, the target nucleic acid is a single-stranded DNA or RNA (e.g., mRNA, siRNA, LncRNA). In certain embodiments, the target nucleic acid has 15 or more nucleotides, e.g., 20, 25, 30, 35, 40, 50, 60, 70, 80, 90, 100, 200, 300, 400, 500, 600, 700, 800, 900, 1000, 2000, 3000, 4000, 5000 or more nucleotides.

As used herein, a "nucleotide sequence" or "polynucleotide sequence" is a polymer of nucleotides (an oligonucleotide, a DNA, a nucleic acid, etc.) or a character string representing a nucleotide polymer, depending on context. From any specified nucleotide sequence, either the given nucleic acid or the complementary nucleic acid sequence can be determined.

The term "oligonucleotide" is used herein to mean a linear polymer of nucleotide monomers. As used herein, the term may refer to single-stranded or double-stranded forms. Monomers making up nucleic acids and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like, to form duplex or triplex forms. Such monomers and their internucleosidic linkages may be naturally occurring or may be analogs thereof, e.g., naturally occurring or non-naturally occurring analogs.

As used herein, a "probe" is an entity that can be used in the detection of a target molecule. Typically, a probe in the present disclosure refers to a nucleic acid molecule, with or without modification. The probe can be both single-stranded and double-stranded nucleotide polymers. Unless indicated otherwise, the probes described in the present application is a single-stranded nucleotide polymer.

The term "sample" as used herein refers to any sample having or suspect of having the target nucleic acid, including sample of biological tissue or fluid origin, obtained, reached, or collected in vivo or in situ. Exemplary biological samples include but are not limited to cell lysate, a cell culture, a cell line, a tissue, an organ, a biological fluid, and the like. In certain embodiments, the sample is a solid sample. In some embodiments, the sample is a tissue.

The term "sequentially" means that the components, domains or regions in a polynucleotide or probe are juxtaposed in a 5' end to 3' end, or 3' end to 5' end order. It is understood that the polynucleotide or probe may include additional nucleotide sequence in adjacent to each component, domain or region or between two components, domains or regions that does not interfere with the function of the polynucleotide or probe.

The term "substrate" refers to a mechanical support upon which material may be disposed to provide functionality, whether mechanical, biological, optical, chemical or other functionality. A substrate may be unpatterned or patterned, partitioned or unpartitioned. Molecules on a substrate may be disposed in features or may be uniformly disposed on the substrate surface.

Spatially Barcoded Microarray

Fabrication of a microarray with spatially barcoded capture probes is critical for spatial transcriptomics. The current barcoding mechanism is based on different combinations of nucleotide sequences in the barcoded region of oligonucleotides, which has low resolution, or is complicated and expensive. The present disclosure in one aspect provides a microarray which is spatially barcoded based on the length of the oligonucleotides (i.e., the number of nucleotides). Such microarray has the advantages of low cost, easy to fabricate, high flexibility in the array dimension and resolution, and high scalability.

An exemplary embodiment of the spatially barcoded microarray described herein is illustrated in FIG. 1. Referring to FIG. 1, the spatially barcoded microarray 100 is composed of a substrate 101, which has a substantially flat surface. In certain embodiments, the substrate is a glass slide.

Referring as to FIG. 1, immobilized on the surface of the substrate 101 is an array of probes, which forms an array area 102. The details of a subset of the array area 102 are illustrated in the inset of FIG. 1. As shown in the inset, a plurality of probes 103 are immobilized on the surface of the substrate. Each probe comprises at least a segment of oligonucleotide. In some embodiments, the probes are covalently linked to the substrate.

Each probe 103 immobilized on the substrate 101 is spatially barcoded, i.e., the location of each probe is traceable or determinable. In some embodiments, each probe 103 comprises at least a segment of oligonucleotide and is barcoded by the length of the oligonucleotide. As provided in detail below, the location of each probe 103 can be determined by the length of oligonucleotides comprised in the probe.

The array area 102 can form any pattern on the substrate 101. In some embodiments, as illustrated in FIG. 1, the plurality of probes are arranged such that the array area 102 forms a shape of square. Other shapes or patterns of arrangement, such as rectangular, circular, oval, triangular, are also contemplated. Notably, the location of each probe immobilized on the substrate 101 can be expressed in a Cartesian (i.e., x-y axis) coordination system. It can be understood that each probe immobilized on the substrate 101 has a different location. In practice, however, depending on the resolution of the spatially barcoded microarray, a group of probes close to each other has the same barcode (e.g., comprising oligonucleotides of the same length) and can be understood as having the same location on the substrate 101.

Figure 2:
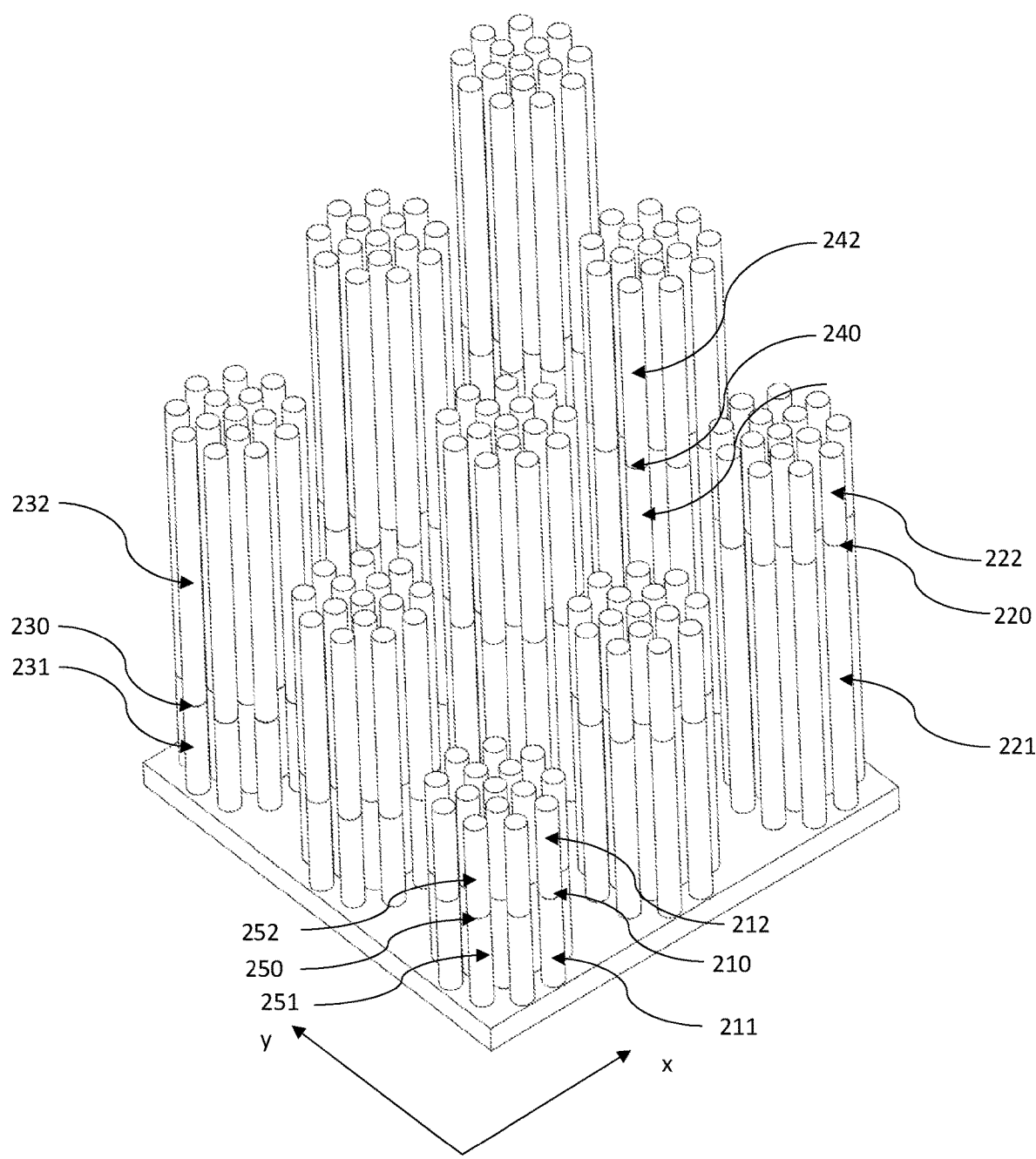
FIG. 2 shows a subset of the array area in a spatially barcoded microarray according to an embodiment of the invention.

FIG. 2 illustrates the barcoding mechanism of an exemplary example of the microarray disclosed herein. Referring to FIG. 2, a subset of the array area comprises a plurality of probes (e.g., 210, 220, 230, 240 and 250) immobilized on the surface of the substrate. Each probe has a barcode region comprising at least two segments of oligonucleotide. For example, referring to FIG. 2, probe 210 comprises oligonucleotides 211 and 212; probe 220 comprises oligonucleotides 221 and 222; probe 230 comprises oligonucleotides 231 and 232; probe 240 comprises oligonucleotides 241 and 242; probe 250 comprises oligonucleotides 251 and 252.

Each probe has a location on the substrate according to a Cartesian coordination system on the surface of the substrate. Referring to FIG. 2, probe 210 has a location $(X_1, Y_1)$ under the Cartesian coordination system; probe 220 has a location $(X_2, Y_2)$; probe 230 has a location $(X_3, Y_3)$; probe 240 has a location $(X_4, Y_4)$. It can be understood that for the purposes of spatially barcoding, probes having distinct locations on the substrate should have distinct barcode, i.e., the identity of the probes is determinable according to the locations of the probes. It can also be understood, however, that a group of probes close to each other (form a cluster or group) may have the same barcode and can be considered as having the same location on the substrate. For example, probe 210 and probe 250 are two probes close to each other and have the same barcode. For the purposes of barcoding, probe 210 and probe 250 are considered as having the same location on the substrate.

As illustrated in FIG. 2, each probe immobilized on the substrate can spatially barcoded based on the length of the two oligonucleotides comprised in the probe. As a principle, the length of the first oligonucleotide comprised in each probe varies according to the location of the probe on the x-axis; and the length of the second oligonucleotide comprised in the probe varies according to the location of the probe on the y-axis. Thus, the combination of the information regarding the length of the first and second oligonucleotides identifies the location of the probe.

In one embodiment, the length of one oligonucleotide comprised in a probe is longer if the probe locates further on the x-axis. As an example, referring to FIG. 2, probe 220 and probe 240 locate further than probe 210 and probe 230 on the x-axis (i.e., $X_2 > X_1$; $X_4 > X_1$; $X_2 > X_3$; and $X_4 > X_3$). Correspondingly, the length of oligonucleotide 221 and oligonucleotide 241 are longer than the length of oligonucleotide 211 and oligonucleotide 231. On the hand, probe 210 and probe 230 have substantially the same position on the x-axis (i.e., $X_1 = X_3$). Correspondingly, the length of oligonucleotide 211 is substantially the same as the length of oligonucleotide 231. Similarly, the length of oligonucleotide 221 is substantially the same as the length of oligonucleotide 241.

In one embodiment, the length of the second oligonucleotide comprised in the probe is longer if the probe locates further on the y-axis. As an example, referring to FIG. 2, probe 230 and probe 240 locate further than probe 210 and probe 220 on the y-axis (i.e., $Y_3>Y_1$; $Y_4>Y_1$; $Y_3>Y_2$; and $Y_4>Y_3$). Correspondingly, the length of oligonucleotide 232 and oligonucleotide 242 are longer than the length of oligonucleotide 212 and oligonucleotide 2. On the other hand, probe 210 and probe 220 have substantially the same position on the y-axis (i.e., $Y_1=Y_3$). Correspondingly, the length of oligonucleotide 212 is substantially the same as the length of oligonucleotide 222. Similarly, the length of oligonucleotide 232 is substantially the same as the length of oligonucleotide 242.

In can be understood that the combination of the length of the first and second oligonucleotides comprised in each probe give rise to a unique barcode of the probe that can identify the location of the probe. For example, referring to FIG. 2, by comparing the length of oligonucleotide 241 with oligonucleotide 211 and comparing the length of oligonucleotide 242 with oligonucleotide 212, it can be determined that probe 240 locates further than probe 210 on both x-axis and y-axis. More comprehensively, the relative position of probes 210, 220, 230 and 240 can be determined based on the information of the length of oligonucleotides 211, 212, 221, 222, 231, 232, 241 and 242.

In certain embodiments, the length of the oligonucleotide comprised in the probe is 1-100 nucleotides, 1-90 nucleotides, 1-80 nucleotides, 1-70 nucleotides, 1-60 nucleotides, 1-50 nucleotides, 1-40 nucleotides, or 1-30 nucleotides. In certain embodiments, the length of the oligonucleotide comprised in the probe is 2-100 nucleotides, 2-90 nucleotides, 2-80 nucleotides, 2-70 nucleotides, 2-60 nucleotides, 2-50 nucleotides, 2-40 nucleotides, or 2-30 nucleotides. In certain embodiments, the length of the oligonucleotide comprised in the probe is 3-100 nucleotides, 3-90 nucleotides, 3-80 nucleotides, 3-70 nucleotides, 3-60 nucleotides, 3-50 nucleotides, 3-40 nucleotides, or 3-30 nucleotides. In certain embodiments, the length of the oligonucleotide comprised in the probe is 4-100 nucleotides, 4-90 nucleotides, 4-80 nucleotides, 4-70 nucleotides, 4-60 nucleotides, 4-50 nucleotides, 4-40 nucleotides, or 4-30 nucleotides. In certain embodiments, the length of the oligonucleotide comprised in the probe is 5-100 nucleotides, 5-90 nucleotides, 5-80 nucleotides, 5-70 nucleotides, 5-60 nucleotides, 5-50 nucleotides, 5-40 nucleotides, or 5-30 nucleotides.

In certain embodiments, each probe has a free 3' end of a nucleotide.

Figure 3:
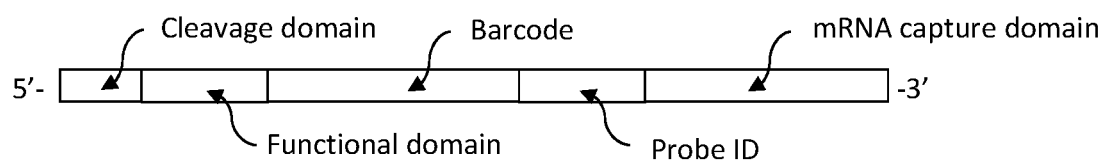
FIG. 3 shows the structure of a probe on a spatially barcoded microarray according to an embodiment of the invention.

In certain embodiments, each probe further comprises cleavage domain, a functional domain, a unique probe identifier, a mRNA capture domain, or a combination thereof. FIG. 3 illustrates the structure of a single exemplary probe. Referring to FIG. 3, a single probe is a single-stranded polynucleotide comprising sequentially from 5' end to 3' end: a cleavage domain, a functional domain (e.g., for amplification and sequencing), a spatial barcode, a probe identifier, and mRNA capture domain. The probe is attached to the substrate at its 5' end. The cleavage domain contains a sequence capable of being recognized by an endonuclease which can release the probe (together with an amplification product generated thereof as discussed infra) from the substrate. In certain embodiments, the functional domain contains sequences that can be used to generate an amplification product for sequencing analysis (see infra for detailed discussion). In certain embodiments, the spatial barcode comprises sequentially from 5' end to 3' end a segment of the first oligonucleotide and a segment of the second oligonucleotide as disclosed supra. In certain embodiments, the probe identifier contains probe-specific sequences that can be used to identify the sample in a multiplex sequencing reaction. In some embodiments, the mRNA capture domain contains a sequence capable of hybridizing to a target nucleic acid which can be used as capture probes for the target nucleic acid from histological slides or individual cells for identifying their spatial information in the application of spatial transcriptomics or single-cell sequencing. In some embodiments, the mRNA capture domain contains a poly-dT oligonucleotide.

Method of Manufacture

The spatially barcoded microarray can be manufactured by the method know in the art, such as microspotting.

In another aspect, the present disclosure provides a method of manufacturing the spatially barcoded microarray disclosed herein. Comparing to the method currently known in the art, the method disclosed herein has the advantages of low cost, easy to fabricate, high flexibility in the array dimension and resolution, and high scalability.

In general, the method of manufacture disclosed herein involves exposing an array of oligonucleotides immobilized on a substrate to an enzyme capable of removing one or more nucleotides from the oligonucleotides. The method involves controlling the number of nucleotides removed from each oligonucleotide based on the location of each oligonucleotide such that the length of the oligonucleotide after treatment of the enzyme represents the location of the oligonucleotide on the substrate.

In one embodiment, the number of nucleotides removed from each oligonucleotide can be controlled by adjusting the timespan in which the oligonucleotide is exposed to the enzyme. In one embodiment, the method involves (a) providing (i) a solid substrate comprising a surface, and (ii) a plurality of first oligonucleotides immobilized on the surface;

(b) exposing the plurality of the first oligonucleotides to a first liquid, wherein the first liquid comprises a first enzyme capable of removing one or more nucleotides from the first oligonucleotides; and (c) controlling the timespan each of the first oligonucleotides is exposed to the first liquid, wherein the number of the one or more nucleotides that are removed from each of the first oligonucleotides correlates with the timespan in which each of the first oligonucleotides is exposed to the first liquid, thereby generating a plurality of probes each having a segment of the first oligonucleotides.

In some embodiments, the timespan each of the first oligonucleotides is exposed to the first liquid increases in the direction of the solid substrate (e.g., along x-axis of a Cartesian coordination system, thereby the length of the segments of the first oligonucleotides forms a gradient along the first direction.

Figure 4:
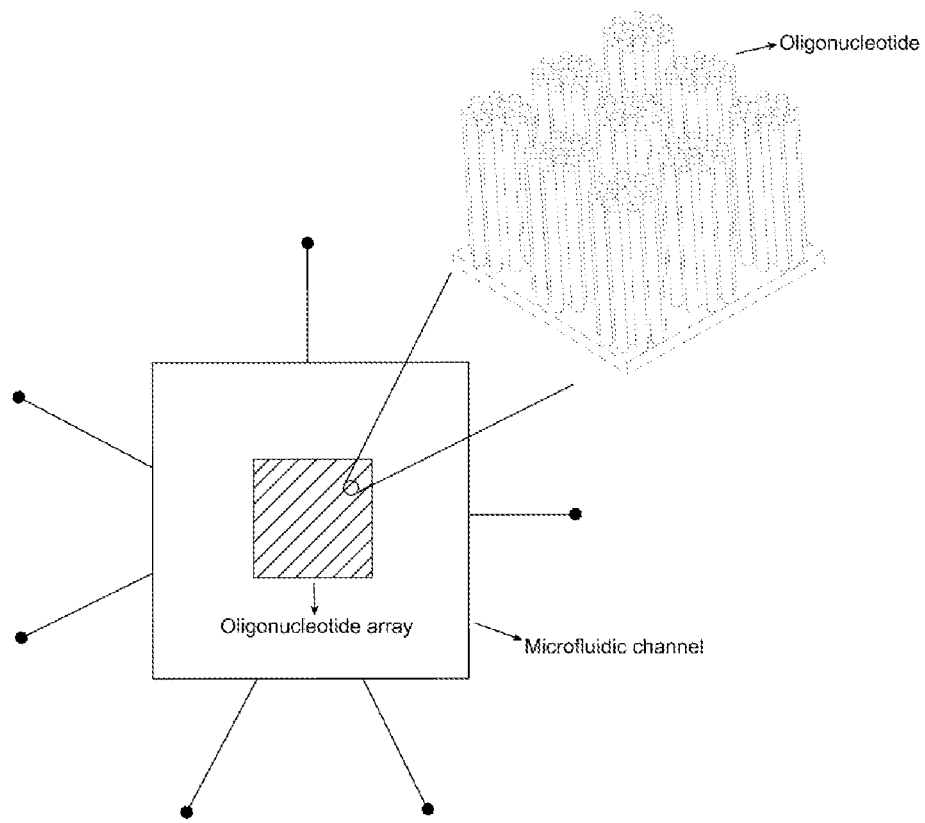
FIG. 4 shows the setup to fabricate a spatially barcoded microarray, which includes a microfluidic channel with six inlets or outlets and a probe array inside the channel, wherein all the oligonucleotides in the probe array have an equal length.
Figure 5:
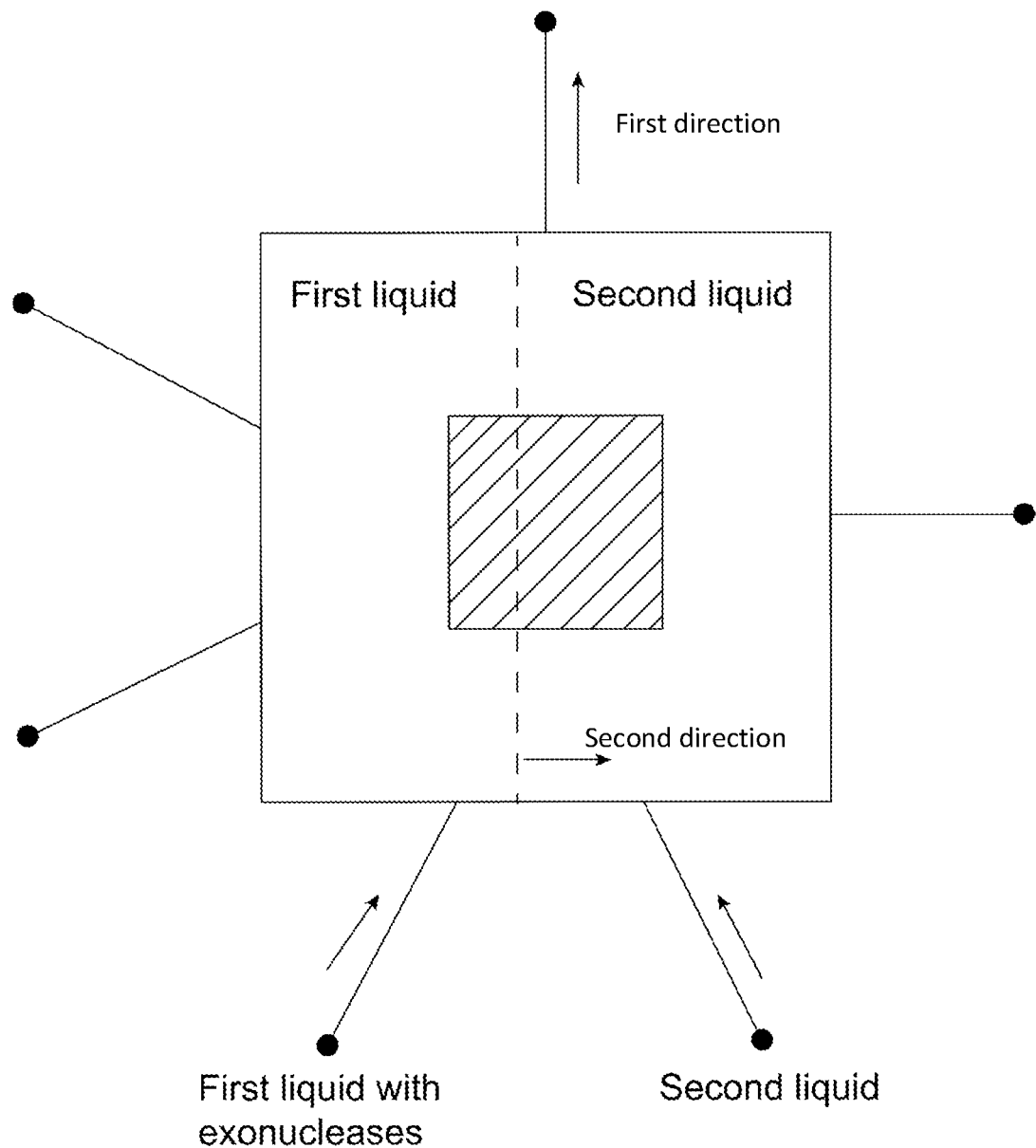
FIG. 5 shows the method of fabricating a one-dimension spatially barcoded oligonucleotide array using the setup illustrated in FIG. 4. The first liquid and the second liquid form a clear and movable interface in the microfluidic channel.
Figure 6:
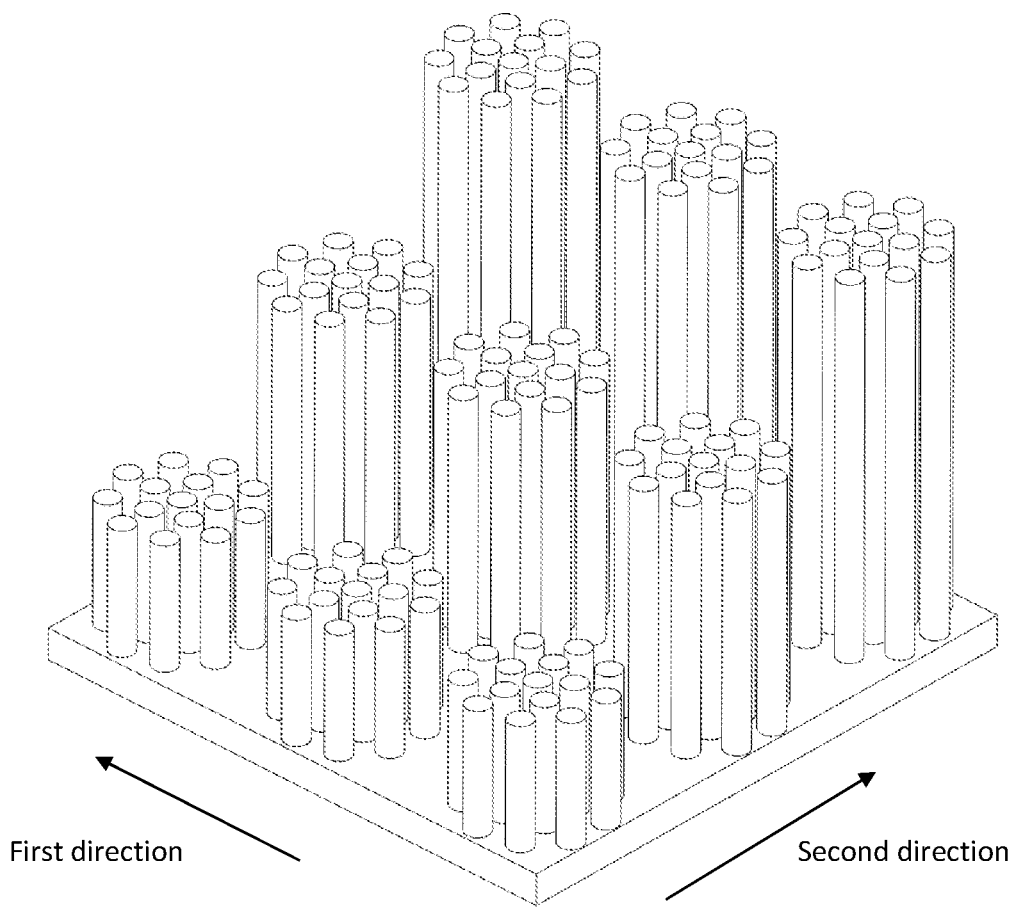
FIG. 6 shows that a one-dimension spatially barcoded oligonucleotide array fabricated by the present method.

In some embodiments, the method of generating a spatially barcoded microarray by controlling the timespan in which the oligonucleotide is exposed to the enzyme can be conducted in a microfluidic channel, which can be understood referring to an exemplary embodiment illustrated in FIGS. 4-6.

FIG. 4 shows an exemplary embodiment of the setup for manufacturing the spatially barcoded microarray. Referring to FIG. 4, the setup for manufacturing the spatially barcoded microarray includes a substrate having a substantially flat surface on which an oligonucleotide array is immobilized. In certain embodiments, all the oligonucleotides immobilized on the substrate have the same sequence or at least the same number of nucleotides. The method of immobilizing oligonucleotides on a substrate is known in the art. For example, Yousefi H et al. teaches several coupling strategies to covalently attach single-stranded nucleic acids to various functional surfaces (Advanced Materials Interfaces (2018) 5: 1800659). See, also, Rashid J and Yusof N, The strategies of DNA immobilization and hybridization detection mechanism in the construction of electrochemical DNA sensor: A review, Sensing and Bio-Sensing Research (2017) 16: 19-31.

Referring to FIG. 4, the setup for manufacturing the spatially barcoded microarray has one or more microfluidic channels, through which liquid can flow across the surface of the substrate. The microfluidic channel has one or more inlets and outlets, through which liquid can flow in or out of the microfluidic channel. The microfluidic channel can be connected to one or more pump modules, which can control the flow rate of the liquid in or out of the microfluidic channel.

As illustrated in FIG. 5, in one embodiment, the oligonucleotides immobilized on the substrate are exposed to a fluidic flow. The fluidic flow comprises a first liquid and a second liquid that is injected to the microfluidic channel from two inlets to form a two-phase flow along a first direction. The first liquid comprises a first enzyme (e.g., an exonuclease) capable of shortening the oligonucleotides by removing one or more nucleotides from the oligonucleotides. The second liquid is an organic solvent such as mineral oil, isophorone, 2-methyltetrahydrofuran (2-MTHF), or cyclopentyl methyl ether (CPME), which is immiscible with the first liquid. The two liquids form a clear interface parallel to the flow direction without molecular diffusion.

The flow rate of the first liquid and/or the second liquid is continuously adjusted, to allow the interface of the two liquids moves in a second direction perpendicular to the first direction and moves from one boundary of the oligonucleotide array to another boundary of the oligonucleotide array as shown in FIG. 5. In this way, the number of the oligonucleotides that are exposed to the exonucleases (in the first liquid) is gradually increased or decreased, resulting in different reaction time for the oligonucleotides at different locations of the array. Because the number of nucleotides that are cleaved from the oligonucleotides is correlated to the length of the reaction time, this process produces an array of oligonucleotides with a length gradient in the second direction (i.e., perpendicular to the first direction) as show in FIG. 6, which results in a one-dimension spatially barcoded oligonucleotide array. By controlling the moving speed of the liquid interface, no oligonucleotide is totally cleaved.

Figure 7:
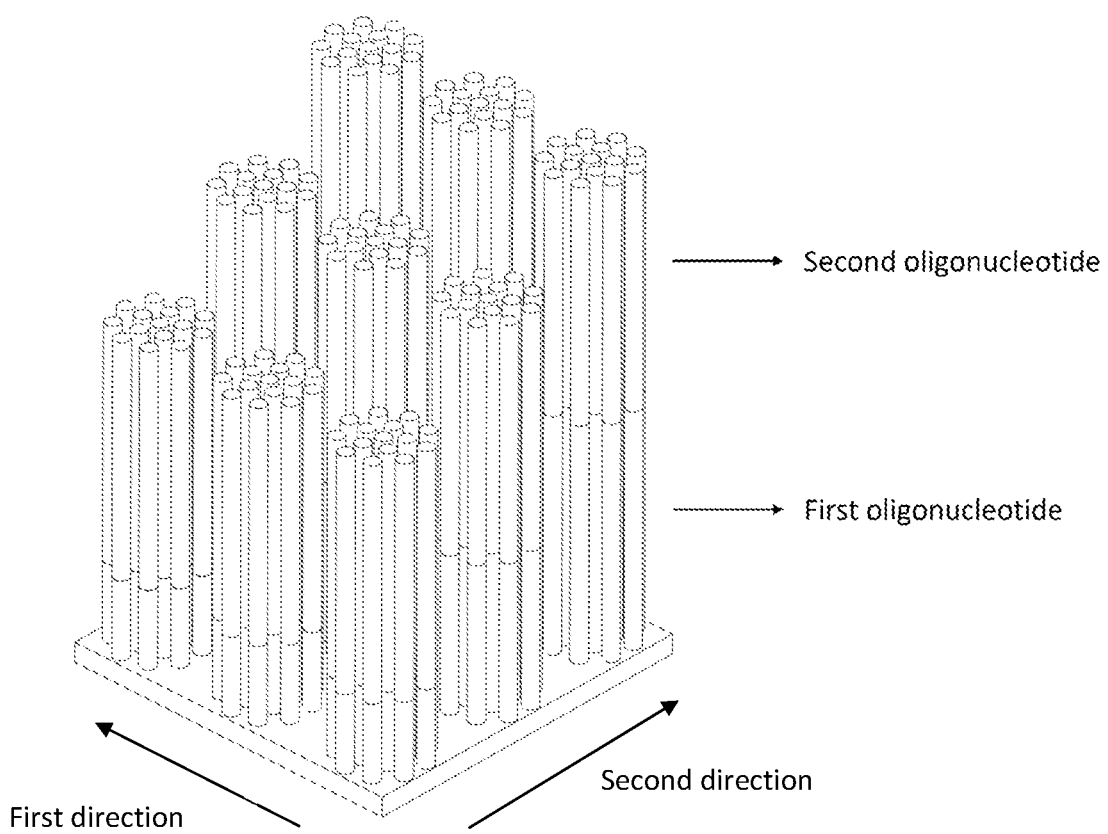
FIG. 7 shows the array after adding a second oligonucleotide to the probes of the one-dimension spatially barcoded oligonucleotide array via ligation.
Figure 8:
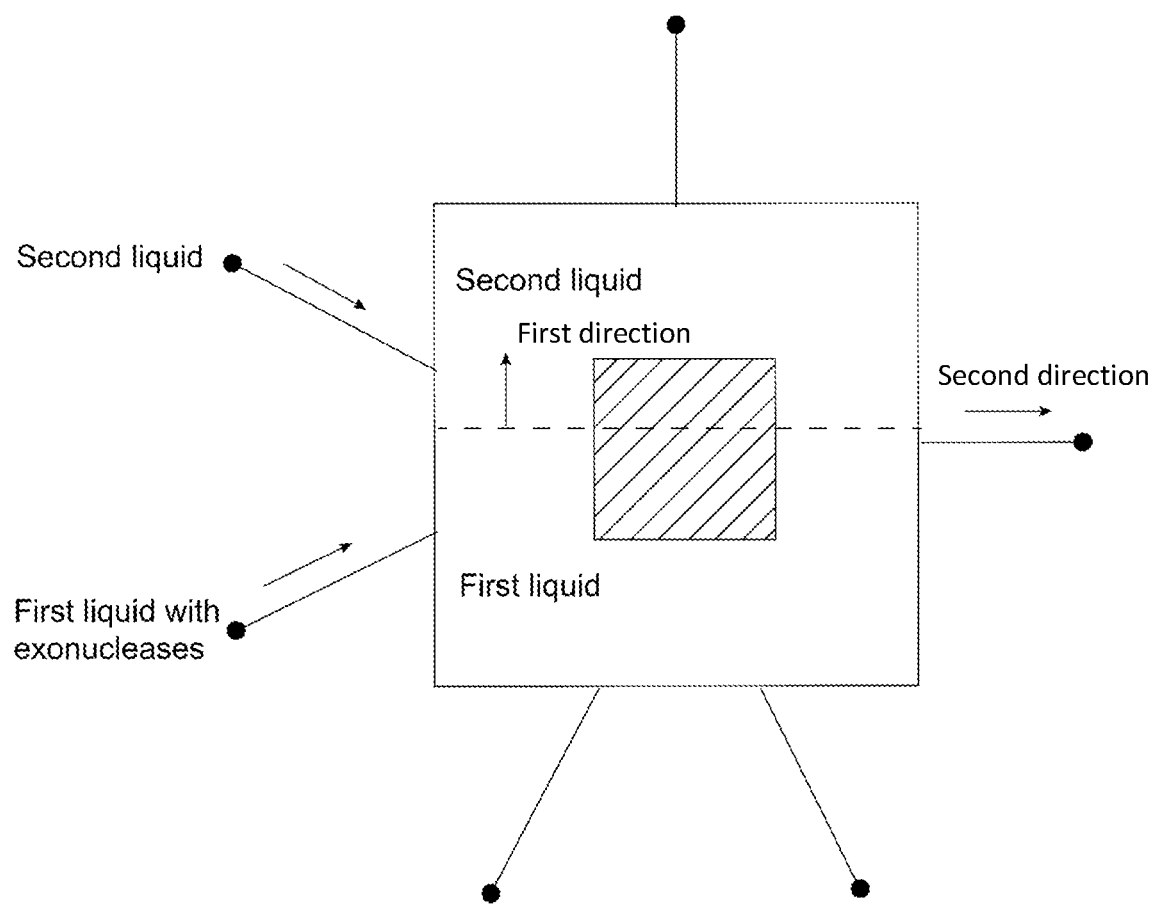
FIG. 8 shows the method to fabricate a spatially barcoded oligonucleotide array in the second dimension by changing the flow direction.

In one embodiment, the one-dimension spatially barcoded oligonucleotide array is further processed to generate a two-dimension spatially barcoded microarray, which can be understood in reference to FIG. 7 and FIG. 8.

Referring to FIG. 7, in order to generate a two-dimension spatially barcoded microarray, a second oligonucleotide is added to the free end of each probe on the one-dimension spatially barcoded microarray described above (each probe comprises a segment of the first oligonucleotide after exonuclease treatment). In some embodiments, the second oligonucleotide can be added by using ligation enzyme. The second oligonucleotide comprises different sequences or different types of nucleotides from the first oligonucleotide, which makes the second oligonucleotide distinguished from the first oligonucleotide by DNA sequencing technology.

FIG. 8 illustrates an exemplary method of generating a length gradient for the second oligonucleotide along the first direction. Referring to FIG. 8, the first liquid and the second liquid are injected from two inlets of the microfluidic channel to generate a two-phase flow in the second direction. By continuously adjusting the flow rate of the first liquid and/or the second liquid, the interface of the two liquid moves along the first direction and moves from one boundary of the oligonucleotide array to another boundary of the oligonucleotide array as shown in FIG. 8. As a result, a length gradient of the second oligonucleotides is generated along the first direction (i.e., perpendicular to the second direction). A two-dimension spatially barcoded microarray combining the first oligonucleotides and the second oligonucleotides (see FIG. 2) is thus generated.

Figure 9:
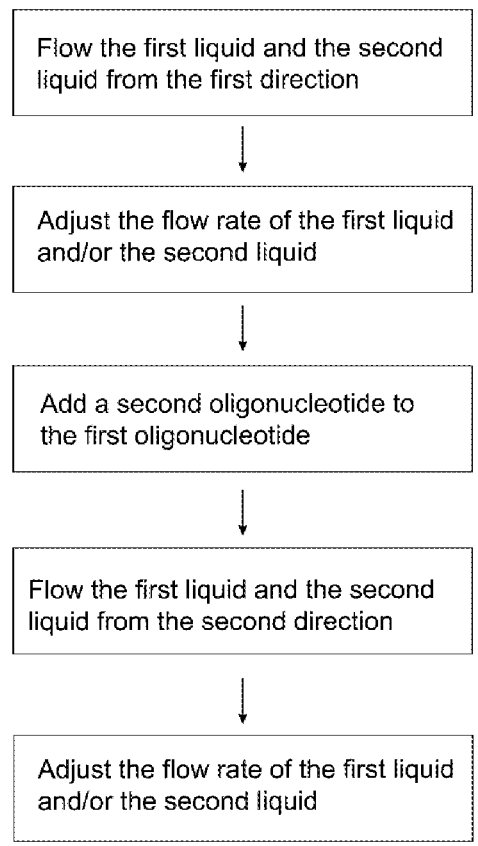
FIG. 9 shows the flow chart of the process to fabricate a two-dimension spatially barcoded microarray according to an embodiment of the invention.

The major steps of manufacturing a two-dimension spatially barcoded microarray disclosed herein can be understood in the flow chart of FIG. 9.

Figure 10:
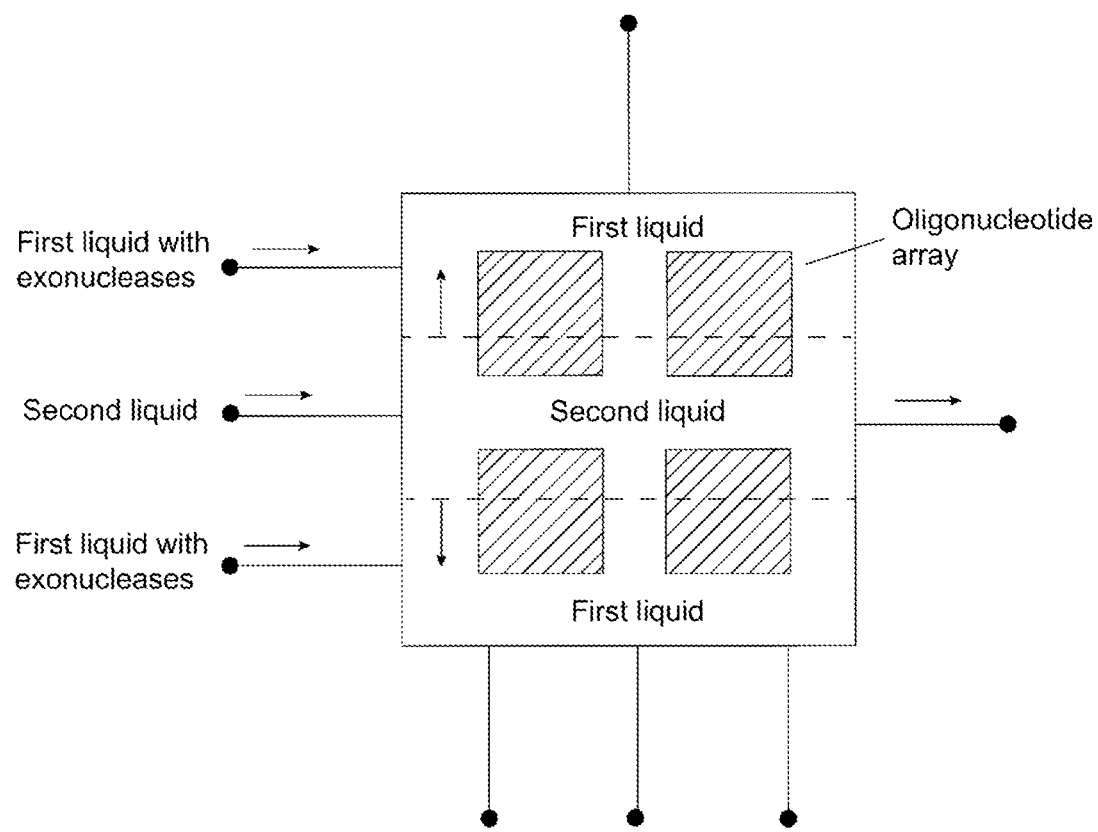
FIG. 10 shows a setup to fabricate four two-dimension spatially barcoded arrays simultaneously.

To scale up the array fabrication, a multiple-phase microfluidic flow comprises one or more the first liquid and one or more the second liquid is created as shown in FIG. 10 to fabricate two or more two-dimension spatially barcoded oligonucleotide arrays simultaneously. Referring to FIG. 10, in a setup of manufacturing a spatially barcoded microarray, first oligonucleotides are mobilized on a substrate to form four oligonucleotide arrays. The oligonucleotides arrays are then exposed to a fluidic flow in a microfluidic channel comprising multiple inlets and outlets. The fluidic flow comprises a first liquid that is injected to the microfluidic channel from two inlets. The fluidic flow also comprises a second liquid that is injected to the microfluidic channel from a middle inlet between the two inlets from which the first liquid is injected. The first liquid comprises a first enzyme (e.g., an exonuclease) capable of shortening the oligonucleotides by removing one or more nucleotides from the oligonucleotides. The second liquid is an organic solvent which is immiscible with the first liquid. The two liquids form a clear interface parallel to the flow direction without molecular diffusion. As a result, a three-phase flow is formed along a first direction.

The flow rate of the first liquid and/or the second liquid is continuously adjusted, to allow the interface of the liquids moves from the middle of the microfluidic channel to the side as shown in FIG. 10. In this way, the number of the oligonucleotides that are exposed to the exonucleases (in the first liquid) is gradually increased or decreased, resulting in different reaction time for the oligonucleotides at different locations of the array. It can be understood that in the setup of FIG. 10, the oligonucleotides located closer to the edge of the substrate will have shorter length as they are exposed to the first liquid for longer time. As a result, four one-dimension spatially barcoded oligonucleotide arrays are generated. Using the same strategy, the one-dimension spatially barcoded oligonucleotide arrays can be further processes to generate four two-dimension spatially barcoded oligonucleotide arrays by injecting the first and second liquid to the microfluidic channel from a different direction (e.g., from bottom to top as shown in FIG. 10).

Figure 11:
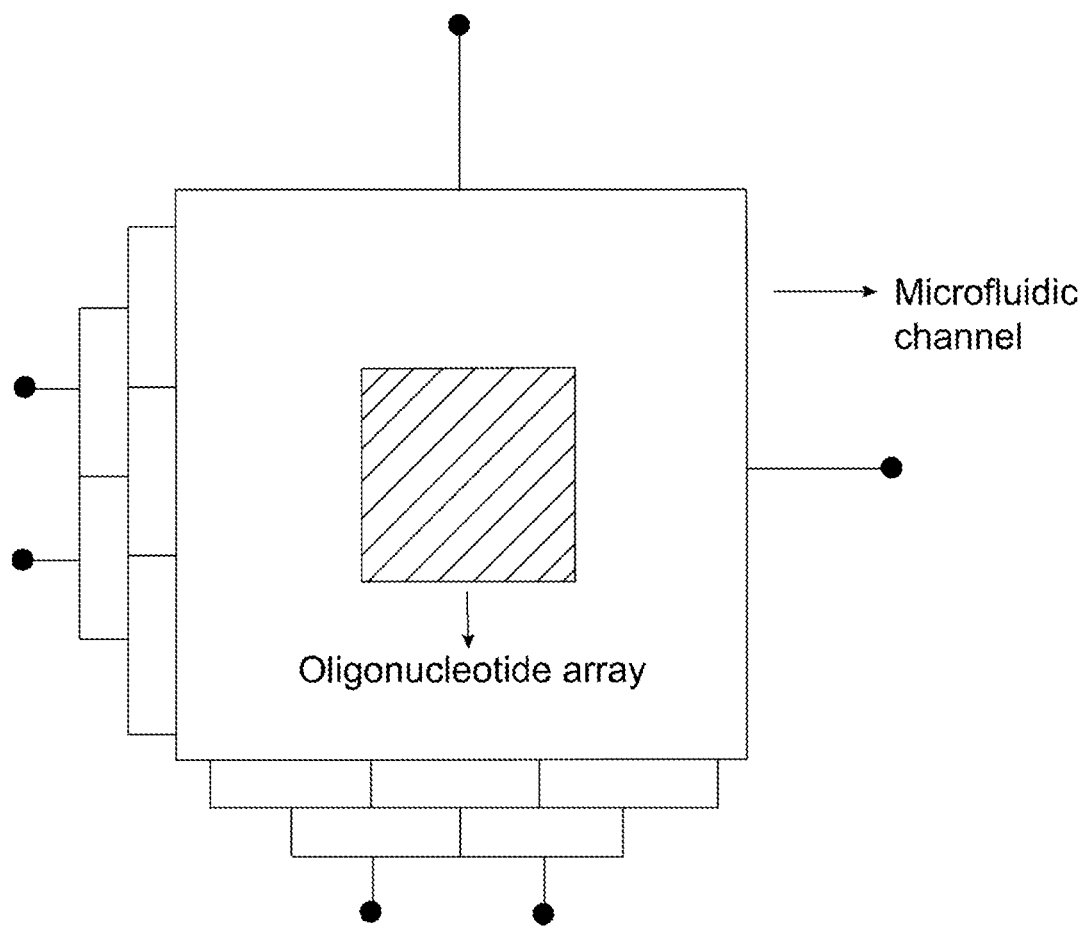
FIG. 11 shows a concentration gradient generator to fabricate a spatially barcoded array.

In another aspect, as illustrated in FIG. 11, a concentration-dependent cleavage process can be used to create a two-dimension spatially barcoded oligonucleotide array. Referring to FIG. 11, concentration gradients of exonucleases are generated via a microfluidic channel with concentration generators. In this setup, the number of nucleotides that are cleaved from the oligonucleotides is correlated to the concentration of the exonucleases at the specific location. For example, when the concentration of the exonuclease forms a gradient in a direction from top of FIG. 11 to the bottom, an array of oligonucleotides with a length gradient from the top to the bottom direction can be generated.

In certain embodiments, the probes in the microarray further comprise a cleavage domain, a functional domain, a unique probe identifier, a mRNA capture domain, or a combination thereof. It can be understood that such probes can be manufactured by sequentially adding relevant domains to the probes during the manufacture process. For example, to manufacture a probe as illustrates in FIG. 3 (which is a single-stranded polynucleotide comprising sequentially from 5' end to 3' end: a cleavage domain, a functional domain, a spatial barcode, a probe identifier, and mRNA capture domain), the manufacture process can start with immobilizing a plurality of foundation oligonucleotides on the substrate, wherein each foundation oligonucleotide comprises sequentially from 5' end to 3' end the cleavage domain, the functional domain and the first oligonucleotide illustrated in FIG. 4. The foundation oligonucleotides immobilized on the substrate are then processed to generate a one-dimension oligonucleotide array as described above. The second oligonucleotides are then added to the 3' end of each probe of the one-dimension oligonucleotide array and processed to generate a two-dimension oligonucleotide array as described above. The probe identifier and mRNA capture domain can then be added to the 3' end of each probe of the two-dimension oligonucleotide array. The method of adding relevant domains to the probe is known in the art, e.g., using a nucleic acid ligase.

Method of Use

In another aspect, the present disclosure provides a method of using the spatially barcoded microarray described herein to measure a biological target (e.g., a nucleic acid target) in a sample. In one embodiment, the method comprises: contacting the sample with a spatially barcoded microarray described herein, allowing the probes to interact with the biological target; extending the probes specifically binding to the biological target to generate a plurality of extended products; and sequencing the plurality of extended products to determine the length of the first barcode oligonucleotide and the length of the second barcode oligonucleotide, thereby identifying the location of each extended product in the sample.

Figure 12:
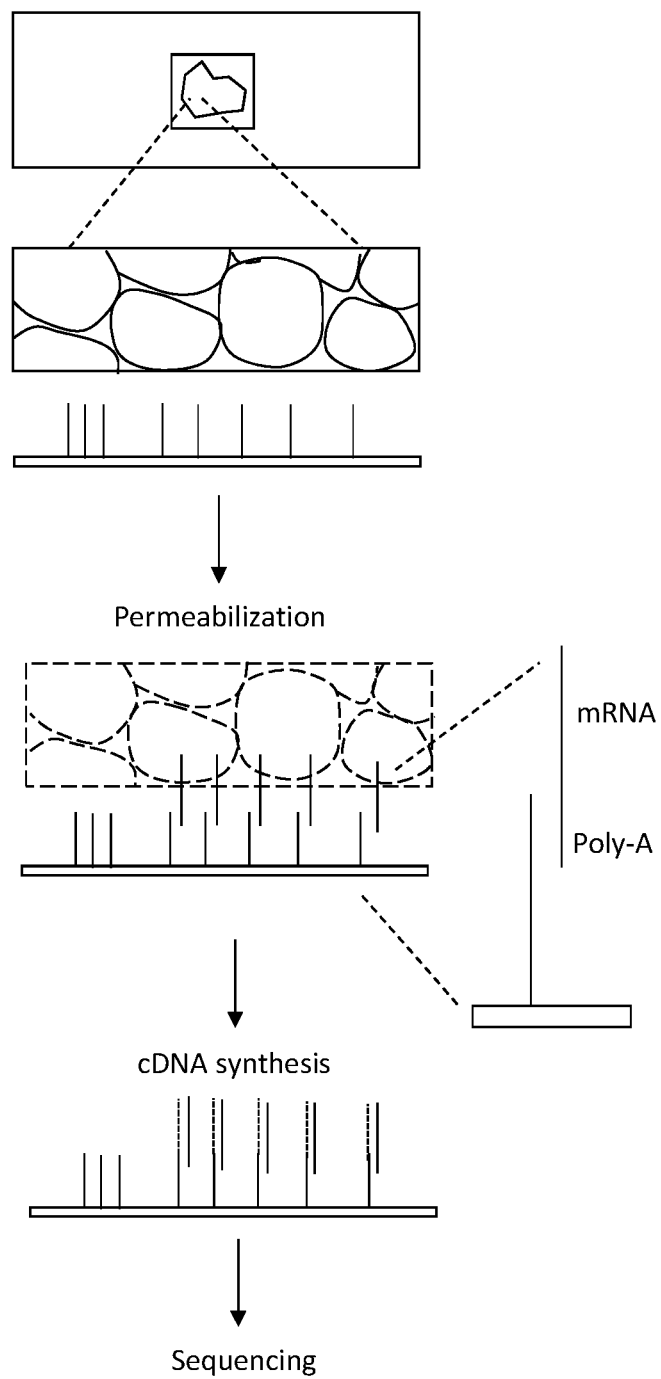
FIG. 12 shows the method of measuring mRNA in a tissue sample using a spatially barcoded microarray according to another embodiment of the invention.

The major steps of an exemplary method of measuring mRNA in a sample are illustrated in FIG. 12. Referring to FIG. 12, to measuring mRNA in a tissue sample, the sample is placed in contact with a spatially barcoded microarray described herein. The tissue is then treated with chemicals to permeabilize the cells and release the mRNA in the cells, such that the mRNA released from the cells interacts with the probes on the microarray. The microarray is then threated with a reaction mix to synthesize the cDNA using mRNA as a template and the probes as primers. The synthesized cDNA is then pooled and prepared for high-throughput sequencing analysis. In certain embodiments, the probes on the microarray have a structure as illustrated in FIG. 3. In such embodiments, the synthesized products can be dissociated from the substrate by cutting the cDNA synthesis products at the cleavage domain of the probes. The cleaved synthesis products are amplified and processes for high-throughput sequencing, e.g., in an Illumina sequencing by synthesis system.

The sequencing results provide information of the cDNA as well as the length of the first oligonucleotide and the second oligonucleotide in the barcode region of the probe. As the length of the first oligonucleotide and the second oligonucleotide in the barcode region is associated with the location of the probe on the microarray, the location of the RNA in the sample can be identified.

What is claimed is:

1. A method for generating a spatially barcoded microarray comprising an array of barcoded probes, the method comprising:
   (a) providing (i) a solid substrate comprising a surface, and (ii) an array of N first initial oligonucleotides of the same length (N is an integer larger than 1,000) immobilized on the surface,
   wherein for any pair of the first initial oligonucleotides consisting of an ith first initial oligonucleotide and a jth first initial oligonucleotide ($1<<i<j<<N$), the ith first initial oligonucleotide has a location of ($X_i$, $Y_i$) under a Cartesian X-Y axis on the surface, and the jth first initial oligonucleotide has a location of ($X_j$, $Y_j$) under the Cartesian X-Y axis on the surface;
   (b) exposing the array of N first initial oligonucleotides immobilized on the surface to a fluidic flow that flows along the Y axis on the surface, wherein the fluidic flow comprises a first liquid and a second liquid that are immiscible with each other and form an interface parallel to the Y axis on the surface, wherein the first liquid comprises an exonuclease, thereby removing one or more nucleotides from each of the array of N first initial oligonucleotides; and
   (c) adjusting the relative proportion of the first liquid and the second liquid in the fluidic flow to move the interface along the X axis on the surface, thereby generating an array of N first barcode oligonucleotides, each first barcode oligonucleotide generated by removing one or more nucleotides from a first initial oligonucleotide,
   wherein for any pair of the first barcode oligonucleotides consisting of an ith first barcode oligonucleotide and a jth first barcode oligonucleotide ($1<<i<j<<N$), the ith first barcode oligonucleotide is generated from the ith first initial oligonucleotide and has the location of ($X_i$, $Y_i$) under the Cartesian X-Y axis on the surface, and the jth first barcode oligonucleotide is generated from the jth first initial oligonucleotide and has the location of ($X_j$, $Y_j$) under the Cartesian X-Y axis on the surface,
   wherein if $X_i$ is larger than $X_j$, then the ith first barcode oligonucleotide is longer than the jth first barcode oligonucleotide.

2. The method of claim 1, further comprising adding a second initial oligonucleotide to each of the first barcode oligonucleotide, thus generating an array of N intermediate probes.

3. The method of claim 2, wherein the second oligonucleotide is added by a first ligase enzyme.

4. The method of claim 2, further comprising exposing the array of intermediate probes to a second fluidic flow that flows along the X axis on the surface, wherein the second fluidic flow comprises a third liquid and a fourth liquid that are immiscible with each other and form a second interface parallel to the X axis on the surface, wherein the third liquid comprises a second exonuclease, thereby removing one or more nucleotides from each second initial oligonucleotide.

5. The method of claim 4, comprising adjusting the relative proportion of the third liquid and the fourth liquid in the fluidic flow to move the second interface along the Y axis on the surface, thereby generating an array of N second barcode oligonucleotides, each second barcode oligonucleotide generated by removing one or more nucleotides from a second initial oligonucleotide, wherein for any pair of the second barcode oligonucleotides consisting of an ith second barcode oligonucleotide and a jth second barcode oligonucleotide ($1<<i<j<<N$), the ith second barcode oligonucleotide is generated from the ith second initial oligonucleotide and has the location of ($X_i$, $Y_i$) under the Cartesian X-Y axis on the surface, and the jth second barcode oligonucleotide is generated from the jth second initial oligonucleotide and has the location of ($X_j$, $Y_j$) under the Cartesian X-Y axis on the surface, wherein if $Y_i$ is larger than $Y_j$, then the ith second barcode oligonucleotide is longer than the jth second barcode oligonucleotide.

6. The method of claim 1, wherein the exonucleases is selected from Exonuclease I, Exonuclease III, Exonuclease V, Exonuclease VII, Exonuclease VIII, Exonuclease T, T5 Exonuclease, T7 Exonuclease, Lambda Exonuclease, and a combination thereof.

7. The method of claim 5, further comprising adding a poly-dT oligonucleotide to the free end of each of the second barcode oligonucleotides.

8. The method of claim 7, wherein the poly-dT oligonucleotide is added by a second ligase enzyme.

9. The method of claim 1, wherein each barcoded probe further comprises a cleavage domain, a functional domain, and a unique probe identifier, or a combination thereof.

10. The method of claim 1, wherein the array of N first initial oligonucleotides is exposed to the fluidic flow in a microfluidic channel and wherein the flow rate of the first liquid and the flow rate of the second liquid are controlled by one or more pump modules.

11. The method of claim 5, wherein the first or third liquid is aqueous phase and the second or fourth liquid is organic phase.

12. The method of claim 1, wherein each of the first initial oligonucleotides is immobilized on the surface via the 5'-end.

\* \* \* \* \*